(12) United States Patent
Laskavy et al.

(10) Patent No.: US 8,497,259 B2
(45) Date of Patent: Jul. 30, 2013

(54) CHOLESTEROL CONTROL AGENT

(76) Inventors: Vladislav Nikolaevich Laskavy, Saratov (RU); Aleksandr Nikolaevich Shokhin, Moscow (RU); Sergei Ivanovich Ivanenko, Moscow (RU)

(*) Notice: Subject to any disclaimer, the term of this patent is extended or adjusted under 35 U.S.C. 154(b) by 0 days.

(21) Appl. No.: 13/523,086

(22) Filed: Jun. 14, 2012

(65) Prior Publication Data

US 2012/0252903 A1   Oct. 4, 2012

Related U.S. Application Data

(62) Division of application No. 12/451,459, filed as application No. PCT/RU2008/000203 on Apr. 2, 2008, now abandoned.

(30) Foreign Application Priority Data

Jul. 4, 2007 (RU) ................................. 2007125298

(51) Int. Cl.
*A01N 43/00* (2006.01)
*A01N 35/02* (2006.01)
*A61K 31/33* (2006.01)
*A61K 31/115* (2006.01)

(52) U.S. Cl.
USPC ........................................ 514/183; 514/694

(58) Field of Classification Search
USPC ................................................ 514/183, 694
See application file for complete search history.

*Primary Examiner* — Marcos Sznaidman
(74) *Attorney, Agent, or Firm* — Aleksandr Smushkovich

(57) ABSTRACT

There is proposed a method for using a preparation for lowering the cholesterol level of a patient. In preferred embodiments, the preparation essentially consists of an active substance being an aqueous solution of formaldehyde with a concentration of 36.5-40%, the active substance constitutes 2-6 weight units, and an additive being an isotonic solution of sodium chloride with a concentration of 0.85-0.95%, the additive constitutes from 998 to 994 weight units accordingly, to make the total of 1000 weight units. The method includes administering the preparation to the patient in the form of intramuscular injections with a predetermined dose at a predetermined time interval, thereby lowering the cholesterol level of the patient. It is preferable to choose the predetermined time interval from the group consisting of 7, 21, 30, and 60 days. It is also preferable to choose the predetermined dose in the amount of 5 mL.

1 Claim, No Drawings

CHOLESTEROL CONTROL AGENT

CROSS-REFERENCE TO RELATED APPLICATIONS

This application is a divisional application in accordance with 37 CFR 1.53 (b) (1) of a U.S. patent application Ser. No. 12/451,459 filed on 13 Nov. 2009 now abandoned, which is a U.S. national stage application of a PCT application PCT/RU2008/000203 filed on 2 Apr. 2008, published as WO2009/005396, which PCT application claims priority of a Russian patent application RU2007/125298 filed on 4 Jul. 2007. This divisional application claims the benefit of U.S. patent application Ser. No. 12/451,459 under 13 U.S.C. 121. The disclosure of U.S. patent application Ser. No. 12/451,459 is hereby incorporated by reference in its entirety. The U.S. patent application Ser. No. 12/451,459 is hereby expressly abandoned.

FIELD OF THE INVENTION

The invention is related to medicine and can be utilized for lowering the cholesterol level of a patient.

BACKGROUND OF THE INVENTION

Blood cholesterol is an important characteristic of lipid metabolism. Cholesterol-lowering therapy provided for patients with atherosclerosis and coronary heart disease results in a reduction of the cardiovascular death rate by 30-40%. There is a direct relationship between blood cholesterol levels and coronary diseases.

Cholesterol-lowering drugs are known which are based on plant preparations. In particular, a cholesterol-lowering drug (see RF Patent No. 2162333 according to IPC A61K35/78, published on Jan. 27, 2001) is known, which contains *Licopodium* (wolfs-claws), Aurum iodatum (auric iodate), Barium carbonicum (barium carbonate), *Alluim sativum* (garlic) taken in equal proportions at CI2 dilution. This drug is a mix of homeopathic preparations, each of these preparations being used for specific indications from arterial hypertension and atherosclerotic processes to chronic liver disease, urolithiasis, adiposity, etc. Use of a multicomponent drug like that described above is equivalent to polyprogmasy which usually makes patient's response to treatment difficult to interpret and ultimately precludes from making up an optimal treatment plan.

Another cholesterol-lowering drug based on plant preparation (see RF Patent No. 2152221 according to IPC A61K35/78, published on Jul. 10, 2000) is known which contains *Salsola Collina* herb dry extract as active substance.

Use of this plant preparation based on *Salsola Collina* is equivalent to the use of a combination of chemical substances because, as stated in the patent description, the active complex contains flavonoids, polysaccharides, carotinoids, sterines, saponins, lipids, amino acids and trace elements. As with above analogue, the variety like this is equivalent to polyprogmasy and will interfere with correct interpretation of patient's response to treatment. Furthermore, the content of active substance in the drug varies from 0.25 to 99.9% which is indicative of a low level of the drug standardization.

Other cholesterol-lowering drugs based on chemical preparations are known. Of particular interest are such drugs as nicotinic acid and its derivatives, bile acids sequestrants, fibric acid derivatives (fibrates), probucol (see Okorokov, A. N. Treatment of Internal Diseases/Practical Guide. Minsk: Vysheshaya Shkola, Vitebsk: Belmedkniga, 1996, vol. 3, book 1, pp. 19-41).

However, treatment with nicotinic acid is associated with a number of side effects, such as liver function impairment, exacerbation of chronic gastritis, gastric ulcer, and also can cause hyperglycemia, skin hyperemia and an elevation of blood levels of uric acid.

Therapy with sequestrants is associated with such side effects as nausea, flatulence, constipation and diarrhea. The treatment can also lead to elevation of triglycerides levels and impairment of digestion of fat-soluble vitamins (A, D, K) and folic acid.

Side effects of the use of fibrates (e.g. bezafibrate, fenophibrate, gemfibrozil) are muscle affection, an increase of lithiasis in biliary tracts, and a possibility to cause leucopenia, thrombocytopenia, and anemia.

Probucol favors ventricular arrythmias, dyspeptic disorders and can increase liver dysfunction.

Lovastatin (synonyms: Mevacor, Lovacor, Medostatin, Recol, Rovacol), a cholesterol-lowering drug, which regulates metabolic processes and contains an active substance of a chemical origin and special-purpose excipients, is the most closely related art drug to the claimed drug (see Vidal's Guide. Drugs in Russia. Moscow: AstraFarmServis, 2000, pp. B-364 to B-365).

The active substance of the related art drug belongs to statins and is [IS(I $\alpha$ (R*),3$\alpha$,7$\beta$,8$\beta$(2S*,4S*),8$\alpha\beta$] 1,2,3,7,8 $\alpha$, -Hexahydro-3,7-dimethyl-8[2-(tetrahydro)-4-hydroxy-6-oxo-2H-pyran-2-yl]-1-naphthalenyl 2-methyl butanoate. The substance acts by inhibiting cholesterol biosynthesis. In the body, lovastatin is metabolized to give $\beta$-oxyacid which is a competitive inhibitor of an enzyme 3-hydroxy-3-methyl-glutaryl coenzyme A (HMG-CoA) reductase.

The related art drug also contains lactose, gelated starch, microcrystalline cellulose, butylated hydroxyanisol, indigotin (E132), and magnesium stearate as excipients.

A drawback of statins, including lovastatin, is that these drugs should be taken for long. Furthermore, statins can affect liver, muscles, gastrointestinal tract, cause sleep disturbances, headaches. In repeated drug administrations, the efficacy of the drug therapy can be reduced (tachyphylaxis) (see Cromwell W. C. Ziajka P. E. Development of tachyphylaxis among patients taking HMG CoA reductase inhibitors./Am J. Cardiol 2000; 86: 1123-1127// The translation is published in CONSILIUM medicum journal, 2001, vol. 3, no. 2. Translated by Elagin, R. I. Razvitie takhifilaksii u patsientov, poluchayushchikh ingibitory HMG-CoA reductasy). In addition, statins show xenobiotic properties.

BRIEF DESCRIPTION OF THE INVENTION

The goal of the present invention is to develop a method for using a physiologically acceptable cholesterol-lowering preparation causing no toxicity and tachyphylaxis. As to the authors' knowledge, no data are available in patents and scientific-technical literature on any drugs lowering cholesterol levels through increasing receptor affinity.

Therefore, there is proposed an inventive method for using a preparation for lowering the cholesterol level of a patient, the aforesaid preparation consists essentially of an active substance in the form of an aqueous solution of formaldehyde with a concentration of 36.5-40%, the aforesaid active substance constitutes from 2 to 6 weight units, and an additive in the form of an isotonic solution of sodium chloride with a concentration of 0.85-0.95%, the aforesaid additive constitutes from 998 to 994 weight units accordingly, to make the total of 1000 weight units; the aforesaid method comprises: administering the preparation to the aforesaid patient in the form of intramuscular injections with a predetermined dose on predetermined days, thereby lowering the cholesterol level of the patient.

The aforesaid predetermined days of administering the intramuscular injections with the predetermined dose are chosen as follows: a first initial day, a seventh day, a twenty first day, a thirtieth day, and a sixtieth day, counting from the first initial day. Efficacy of the treatment was evaluated on the 7th, 28th, 35th and 65th days, counting from the first initial day.

Formaldehyde is known to be a natural product of cellular metabolism (see Hunter B. K. et al. Formaldehyde metabolism by *Escherichia coli*. Carbon and solvent deuterium incorporation into glycerol, 1,2-propanediol and 1,3-propanediol.// Biochemistry, 1985, vol. 24, no. 15, pp. 4148-4155). Formaldehyde is produced as a result of metabolic activities from alcohols and amino acids in eukaryotes and prokaryotes and found in cells either free or bound to other metabolites, primarily, to tetrahydrofolate and glutathione. Formaldehyde is also known to be used as immune-modulator (see RF Patent No. 2077882 according to IPC A61K31/115, published on Apr. 27, 1997).

The mechanism of regulation of blood cholesterol is based on the ability of formaldehyde, discovered by the authors, to trigger a hypermutation mechanism, which leads to an increase of the affinity of receptors regulating the cholesterol levels.

The instant authors have established experimentally that introduction of formaldehyde 'in vitro' leads to a decrease of the level of the transforming growth factor, which provokes apoptosis or programmed cell death. Apoptosis participates in pathogenesis of atherosclerosis of heart coronary vessels (see, for example, Storozhakov G. I., Uteshev D. B. Apoptosis' role in the development of atherosclerosis, myocardial ischemia and cardiac insufficiency/Cardiac insufficiency—2000.—vol. 1.—No. 4). In pathogenesis of atherosclerosis one of the important aspects is impairment of endothelium function. Now endothelium dysfunction is understood as (see, for example, Cherkashin D. V. Clinical significance and correction of endothelium function—htt:/www. Cardiolog.ru) imbalance between mediators providing normally optimal course of all endothelium depending processes, including also the transforming growth factor, relating to prosclerous cytokines (see, for example, Cooper M. E., Rumbler Y., Komers R. et. al.—Diabets.—1994. No. 43—P. 1221-1228).

At that not only abnormal cells of vascular walls but also of other tissues such as liver, thyroid, adrenals are exposed to apoptosis. This, in turn, results in functional recovery of the organs, including reactivation of enzymes responsible for lipid breakdown, and normalization of a physicochemical condition of blood proteins which, ultimately, leads to normalization of the blood cholesterol levels.

An aqueous solution of formaldehyde is a transparent colorless liquid with a specific sharp odor, miscible with water and alcohol in all proportions.

Formaldehyde belongs to the class of aldehydes HCOH and is a colorless gas with a sharp odor, having a molecular weight of 30.03, density (at 20° C.) of 0.815, melting point of −92° C. and boiling point of −19.2° C. It is well soluble in water and alcohol. The substance is easily polymerized to form paraformaldehyde in an aqueous medium or polyoxymethylene in non-aqueous media (butane, hexane).

Isotonic solution of sodium chloride for injections is a colorless liquid with saline taste. The solution is sterile and apyrogenic.

Sodium chloride is cubic crystals or white crystalline powder with saline taste, odorless and soluble in water (1:3).

The claimed preparation (cholesterol control agent) is a transparent colorless solution, that is odorless slightly saline in taste.

DETAIL DESCRIPTION OF PREFERRED EMBODIMENTS OF THE INVENTION

While the invention may be susceptible to embodiment in different forms, there are described in detail herein, specific embodiments of the present invention, with the understanding that the present disclosure is to be considered an exemplification of the principles of the invention, and is not intended to limit the invention to that as exemplified herein.

The Preparation and Method of Using Thereof.

The preparation is preferably made in the following way:

Take 2-6 weight parts of 36.5-40% medicinal solution of formaldehyde, add it to 998-994 (accordingly to make the total of 1000 weight parts) weight parts of sterile 0.85-0.95% solution of sodium chloride for injections to receive 0.07-0.24% solution of formaldehyde. The preparation should be stored in a dark place at temperature of 15-35° C.

EXAMPLE 1

Take 0.2 ml of 37% medicinal solution of formaldehyde, add it to 99.8 ml of sterile 0.9% (or 0.95%) isotonic solution of sodium chloride. The so obtained solution mixture is stirred thoroughly. The final concentration of formaldehyde in the received preparation will make 0.074 mass %.

EXAMPLE 2

Take 0.6 ml of 37% medicinal solution of formaldehyde, add it to 99.4 ml of sterile 0.9% (or 0.95%) isotonic solution of sodium chloride. The so obtained solution mixture is stirred thoroughly. The final concentration of formaldehyde in the received preparation will make 0.222 mass %.

EXAMPLE 3

Take 0.6 ml of 40% medicinal solution of formaldehyde. Make the preparation according to the method described in example 2. The final concentration of formaldehyde will make 0.24 mass %.

EXAMPLE 4

Take 3 ml of 40% medicinal solution of formaldehyde, add it to 997 ml of sterile 0.95% isotonic solution of sodium chloride. The so obtained solution mixture is stirred thoroughly. The final concentration of formaldehyde in the received preparation will make 0.12 mass %.

Experiments on Toxic Effect

To prove the absence of any toxic effect of the claimed preparation, experiments on mice were performed.

The experimental study was conducted on 56 outbreed ICR male and female mice weighing 18 to 24 g. The experimental animals were kept in a standard living and care environment of a vivarium on steady diet and provided with unlimited access to water and feed.

Animal observations were carried out during 14 days post administration of the preparation. During the follow-up period, general condition, motor activity, behavior, reaction to stimuli and reflexes were assessed. When required by the protocol of experiments, animals were weighted and consumptions of food and water were determined. The animals, died during the experiments, were dissected and an assessment of changes was made and organ weight ratios were determined (brain, liver, heart, spleen, kidneys, adrenals, testicles, ovaries). The survived animals were crucified at the end of the follow-up period by dislocation of the cervical spine and dissected. A postmortem examination was conducted to assess macroscopic changes of the internals, if any.

Toxicity was assessed by the Litchield and Wilcoxon method of probit analysis using S. Rot's nomograms.

The preparation containing 0.2 mL of 37% formaldehyde solution and 99.8 mL of 0.9% sodium chloride solution was administered once intramuscularly at doses of 5, 25 and 50 mL/kg body weight. During the follow-up period, test animals were weighted trice (1, 7 and 14 days post dose administration).

The study did not reveal any changes in general condition and behavior of the test animals after injection of the preparation at a dose of 5.0 mL/kg. There was no case of animal death during the follow-up period. Weight gains were within the normal range. No difference was found in general condition and behavior between male and female animals.

In the 25 mL/kg group, the picture was close to that described above. General condition, behavior, food and water consumptions, weight gains were within normal ranges both in male and female animal subgroups.

In the 50 mL/kg group, animals showed a short-term (lasting up to 1 min) slight agitation, but after that the condition of the animals in this group did not differ significantly from that in other experimental groups.

At the end of the follow-up period (14 days post dose administration), test animals were crucified by dislocation of the cervical spine, dissected and subjected to macroscopic examination. After that, the internals were removed, weighted and organ weight ratios were determined. The post mortem study showed that organ weight ratios did not differ significantly between experimental groups and were within normal ranges. No local reactions (infiltrate, hyperemia, hair loss, etc.) were observed.

In another study, the preparation was administered at a concentration as high as 10 times the strength of drug product, i.e. containing 2 mL of 37% formaldehyde solution and 98 mL of 0.9% sodium chloride solution.

The preparation was administered i.m. to ICR mice (male and female) at doses of 6, 12.5 and 25 mL/kg.

During the first 5-6 hours post dose administration, test animals showed a moderate depression of excitability and reactivity. There was a gradual acceleration of breathing and heart beating. However, no case of animal death was registered during the first 24 h post administration of the preparation. Only one mouse died from respiratory arrest on day 4 post administration of the dose of 25 mL/kg.

Post dose administration, all animals developed a local reaction as muscular tissue induration. At the end of the experiment, hair loss and formation of dense infiltrate were seen at the site of injection.

The study showed that the initial toxic dose did not have any significant influence on weight gain of the test animals. Variations of the values of weight gain in male and female groups were within limits of tolerance.

At the end of the experiment, test animals were crucified and subjected to macroscopic examination, the internals were removed, weighted and organ weight ratios were calculated.

The study showed that in test animals, both male and female, who received the preparation at a dose as high as 10 times therapeutic dose, organ weight ratios for brain, heart, liver, spleen, kidney, adrenals, testicles (ovaries) at the end of study period did not differ significantly from respective normal values in general population.

Thus, the results obtained suggest a low toxicity of the applied preparation.

Inventive Method of Treatment

The inventive method of treatment of a patient in preferred embodiments consists in that the inventive preparation is administered as intramuscular injections of a predetermined dose, preferably of 5 mL, at predetermined days, preferably: on the initial 1st day, 7th day, 21st day, 30th day, and 60th day, counting from the initial 1st day.

To measure the cholesterol levels in patients, venous blood samples were taken from the ulnar vein in the morning hours.

The clinical study of the preparation was conducted at Republican Infectious Hospital of the Republic of Belarus (Minsk) in compliance with principles of Declaration of Helsinki, requirements of international ethic standards and scientific standards of quality and design of studies involving human subjects, Public Health Law of the Republic of Belarus and Order of the Ministry of Health of the Republic of Belarus No. 254 dated Aug. 18, 2000 *On Conducting Clinical Studies of Drugs*.

Efficacy of the treatment was determined 7, 28, 35 and 65 days post dose administration. Patients with cholesterol levels up to 5.2 mM/L are considered normal (see Okorokov, A. N. Treatment of Internal Diseases/Practical Guide. Minsk: Vysheshaya Shkola, Vitebsk: Belmedkniga, 1996, vol. 3, book 1, pp. 19-41), from 5.2 to 6.2 mM/L moderately and higher than 6.2 mM/L heavily hypercholesterinemic.

The results of cholesterol level correction are given in Table 1.

TABLE 1

Treatment efficacy (n = 20)
Blood serum cholesterol levels, mM/L

| Baseline (M ± m) | 7 days post dose administration (M ± m) | 28 days post dose administration (M ± m) | 35 days post dose administration (M ± m) | 65 days post dose administration (M ± m) |
|---|---|---|---|---|
| 4.35 ± 0.26 | 4.67 ± 0.45 | 5.31 ± 0.46 | 3.58 ± 0.15 | 3.17 ± 0.18 |

$P < 0.05$ for differences between days 35 and 65 and baseline.

Data presented in Tables 2 and 3 are demonstrative of the efficacy of treatment in patients with moderate and heavy hypercholesterinemia.

TABLE 2

Results of treatment of moderately hypercholesterinemic patients

Blood serum cholesterol levels, mM/L

| Patient | Baseline | 7 days post dose administration | 28 days post dose administration | 35 days post dose administration | 65 days post dose administration |
|---|---|---|---|---|---|
| K. | 5.4 | 8.5 | 8.5 | 4.6 | 3.6 |
| P. | 5.7 | 4.3 | 3.0 | 2.8 | 4.6 |

TABLE 3

Results of treatment of heavily hypercholesterinemic patients

| Patient | Baseline | 7 days post dose | 28 days post dose | 35 days post dose | 65 days post dose |
|---------|----------|------------------|-------------------|-------------------|-------------------|
| | | Blood serum cholesterol levels, mM/L | | | |
| V. | 6.8 | 7.3 | 4.6 | 3.08 | 2.8 |
| O. | 6.8 | 3.3 | 4.6 | 3.2 | 1.96 |

Thus, the above disclosed preparation lowers blood cholesterol levels without causing toxicity and tachyphylaxis.

We claim:

1. A method for lowering cholesterol levels in patients in need thereof; said method including: providing an intramuscular injection of 5 ml of a composition comprising:
   (a) 2-6 units of a 36.5-40% formaldehyde solution in water, and
   (b) 998-994 weight units of a 0.85-0.95%, sodium chloride aqueous solution, for a total of 1000 weight units;
wherein said intramuscular injection is administered on a first initial day, and thereafter, counting from the first day: on a seventh day, on a twenty first day, on a thirtieth day, and on a sixtieth day.

* * * * *